US00PP13661P29

(12) United States Plant Patent
Vardi et al.

(10) Patent No.: US PP13,661 P2
(45) Date of Patent: Mar. 18, 2003

(54) CITRUS TREE NAMED 'MERAV'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL); Hana Neumann, Hemed (IL)

(73) Assignee: State of Israel-Ministry of Agriculture and Rural Development, Tel Aviv (IL)

( * ) Notice: Subject to any disclaimer, the term of this patent is extended or adjusted under 35 U.S.C. 154(b) by 0 days.

(21) Appl. No.: 09/716,984

(22) Filed: Nov. 20, 2000

(51) Int. Cl.[7] ..... A01H 5/00

(52) U.S. Cl. ..... Plt./202
(58) Field of Search ..... Plt./202

(56) References Cited

PUBLICATIONS

GTITM UPOVROM Citation for 'Merav'as per IL PBR 02643; Feb. 26, 1999.*

* cited by examiner

*Primary Examiner*—Kent L. Bell
(74) *Attorney, Agent, or Firm*—Akerman Senterfitt

(57) ABSTRACT

A new variety of mandarin citrus is described that is distinguished by fruit having few or no seeds and a mid late fruit ripening period.

2 Drawing Sheets

FIELD OF THE INVENTION

A new mandarin citrus tree *Citrus reticulata* hybrid is described. The new variety named 'Merav' is desirable to the consumer because of the orange color of its fruit and to the commercial grower because of its mid-season fruit ripening at the end of December to January.

BACKGROUND OF THE NEW TREE

The present invention relates to a new and distinct variety of mandarin citrus tree *Citrus reticulata* hybrid developed by inventors Aliza Vardi, Pinchas Spiegel-Roy, Avraham Elchanati, Ahuva Frydman-Shani and Hana Neumann in Bet Dagan, Israel from a controlled pollination cross between 'Wilking' mandarin as seed parent and 'Michal' as a pollen parent.

Asexual reproduction by conventional bud grafting of the new variety at the Agriculture Research Organization Volcani Center in Bet Dagan, Israel, has shown that the new characteristics are stabilized and permanently fixed through successive propagation.

The objective in breeding the present new tree variety, assigned the denomination 'Merav', was to obtain high quality citrus mandarins with few or no seeds. In the spring of 1978, the seed parent 'Wilking' (unpatented) mandarin from a cross of 'King'×'Willowleaf' (Mediterranean) reported by Frost in Calif. Agr. Exp. Sta. Bull. 1935, pp.597–601, was crossed with pollen parent 'Michal' (unpatented), a cultivar of Israeli origin believed to be a natural hybrid between two *Citrus reticulata* Blanco cultivars. The fruits were collected in November 1978. Seeds were extracted and germinated in January 1979. About 400 seedlings were grown from the germinated seeds. The seedlings were grafted onto Troyer orange nucellar rootstock and planted in 1980 in the Agriculture Research Organization experimental grove, Bet Dagan, Israel. The first fruits were observed in December 1984 and again in 1985.

One of the 360 plants was designated observed to be fully ripe in the last week of December and to the end of January. The fruit was observed to be orange in color with several seeds.

Bud wood was taken from k/32/79 and top grafted in the spring of 1986 on 2 Troyer rootstock in the experimental grove of the Agricultural Research Organization, Bet Dagan, Israel. The first crop of these trees was obtained in 1989. The yield of the scion grafted onto Troyer rootstock was good. The fruit was fully ripe the last week in December. The color of the fruit when fully ripe was dark orange, and the fruit was quite easy to peel. The fully ripe fruit had excellent flavor and the juice had a sugar concentration of about 17.3% and an acid content of about 1.34%

SUMMARY OF THE INVENTION k/32/79, designated 'Merav', is characterized by fruit having several seeds and flowers with anthers bearing semi fertile pollen. It is similar in leaf canopy and leaf shape to 'Michal' mandarin. Table 1 shows some of the characteristics of the new tree compared to the seed parent 'Wilking' and pollen parent 'Michal'. Color designations have been determined from The R.H.S. Colour Chart published by The Royal Horticultural Society, London.

TABLE 1

| Tree | Fruit skin color | Chromosome number | Seeds/fruit | Pollen fertility[1] |
|---|---|---|---|---|
| k/32/79 'Merav' | Orange 30B | 2n = 18 | 0–9 | 55% |

TABLE 1-continued

| Tree | Fruit skin color | Chromosome number | Seeds/fruit | Pollen fertility[1] |
|---|---|---|---|---|
| 'Wilking' | Orange RHS 25A | 2n = 18 | 6–15 | 94% |
| 'Michal' | Orange-red RHS 33A | 2n = 18 | 2–9 | 86% |

[1]Estimated by Acetocarmine staining

The following is a detailed description of the new mandarin citrus variety based on observations made under typical Israeli grove conditions.

The tree shape, size and leaf canopy are similar to 'Michal' mandarin. Young shoots have no anthocyanin coloration at the tip. The tree is very productive with a slight tendency to alternate bearing (lower yield of fruit after a year of heavy bearing if fruit is not harvested). The canopy is moderately dense. The bark of the young shoots is initially smooth and green, gradually turning into a smooth yellow-green.

The chromosome number of the tree is diploid (2n=18) as is the chromosome number of the two parents.

The leaf blade is short to medium and the width is narrow. The leaf shape in cross section is slightly concave. Foliar flushes, as measured in Bet Dagan, Israel, occur between April and September and the leaves have medium green color. The firmness of the leave blade is weak. Petioles are short and wingless.

The characteristics of the flowering and the flower parts are short and resemble both parents. Flowering as measured in Bet Dagan, Israel, occurs between mid March and the beginning of April. Terminal flower buds have no anthocyanin coloration. Anther color is yellow with 55% stainable pollen grain as obtained by staining with acetocarmine. All flowers of mandarin cultivars are very much alike in color, anthers, pistil, etc. except that the flower size can be somewhat different.

The fruit has few seeds, about 0–9 seeds per fruit. The fruit shape is oblate and medium in size. When 50 fruits were measured, the fruit had an average weight of 110 grams, an average height of 53 mm, and an average diameter 60.5 mm. The fruit surface is usually smooth with a dark-orange color, 30B, on The Royal Horticultural Society of London Colour Chart. Fruit ripening does not differ from outside of the canopy to the inside, but the fruit color of the outside canopy is a little brighter compared to the fruit color of the inside canopy. There is no persistence of the style and the areola is not completely developed. A navel is absent. The rind is thin and relatively easy to peel.

The color of the albedo is white and the flesh is orange in color. The fruit contains 10–11 segments and is juicy. The external color of the seeds is yellowish. The color of the cotyledons is white. The seed size is medium. The fruit reaches maturity in last week of December–January in Israel. The ripening of the fruit on the tree and within the fruit is uniform. Fruit remains on the tree does not re-green and does begin to loose quality in mid February. The fruit has attractive appearance and excellent flavor.

Although 'Merav' and 'Shani' (U.S. Plant patent application Ser. No. 09/716,483) are sibling cultivars, they can be distinguished from each other as shown in Table 2.

TABLE 2

| | Time of Ripening | Fruit skin color | Fruit flavor |
|---|---|---|---|
| 'Merav' | December–January | orange RHS 30B | excellent |
| 'Shani' | February–mid March | orange-red RHS 34A | excellent excellent aroma |

DESCRIPTION OF THE PHOTOGRAPHS

The new citrus tree is illustrated in the accompanying color photographs.

Sheet one depicts the whole tree and canopy shape of the new variety.

Sheet two shows the exterior of the fruit as well as transverse midsections in a plane substantially perpendicular to the axis, illustrating one seed in the interior of the fruit.

DESCRIPTION OF THE NEW TREE

The following is a detailed description of the new mandarin citrus variety 'Merav' based on observations made under typical Israeli grove conditions. Observations were made on 4–5 year old citrus.

Tree:

*Origin.*—Cross between seed parent 'Wilking' and pollen parent 'Michal'.

*Classification.*—Botanical: *Citrus reticulata* hybrid. Common: Mandarin citrus. Cultivar: 'Merav'.

*Shape.*—Medium in size, somewhat round.

*Thorns.*—Thorns 1–10 mm length.

*Branching.*—Upright.

*Canopy.*—Moderately dense.

*Bark.*—Immature: Smooth, green, RHS 137A. Mature: Smooth, yellow-green, RHS 148A.

*Leaf.*—Size: Narrow width, 36 mm, length 78 mm. Leaf blade: Short to medium, cross section slightly concave taper-pointed. Petioles: Wingless 12 mm length, 1.5 mm in diameter, Green RHS 146B. Color: Upper surface: Green RHS 146A; lower surface: Green RHS 146B. Firmness: Weak. Foliar flushes: April–December.

*Habit.*—Moderately vigorous.

*Height.*—2.5–3 m.

*Trunk diameter.*—18 cm at 20 cm above the ground.

*Spread.*—Depends on proximity in grove and pruning.

*Disease resistance.*—No particular susceptibility or resistance observed.

*Winter hardiness.*—Winter temperature in Bet Dagan, Israel averages 4–7 degrees Centigrade.

Flower:

*Petals.*—5.

*Petal color.*—White RHS 155C.

*Flowering period.*—Mid March to early April (Israel).

*Flower drop.*—April.

*Stamens.*—Approximately 20 with complete style development.

*Anther color.*—Yellow, RHS 12C.

*Pollen fertility.*—55% by acetocarmine staining.

*Anthocyanin coloration.*—No coloration.

Fruit:

*Shape.*—Oblate.

*Size.*—Medium.

*Weight.*—110 g (average of 50 fruits).

*Height.*—53 mm.

*Diameter.*—60.5 mm.

*Surface color.*—Orange RHS 30B.

*Rind oil gland.*—About 40/cm$^2$.

*Style.*—About 6 mm length.

*Navel.*—Absent.

*Rind.*—Thin (2 mm) and easy to peel.

*Albedo.*—Yellow-white RHS 158B.

*Areola.*—Not completely developed.

*Fruit segments.*—10–11.

*Color of flesh.*—Orange RHS 28A.

*Time to maturity.*—End of December, January (Israel); picking at end of December through January.

*Productivity.*—60 kg per tree each season at age 6.

*Fruit extract.*—(Quality tested Jan. 10, 1994). Total soluble solids (TSS): 17.5%. Acid content: 1.34%. TSS/acid ratio: 13. Flavor: Pleasant.

Seeds:

*Size.*—Medium.

*Color.*—External: Yellow-white RHS 158A. Internal: Grey-brown RHS 199C.

*Cotyledons.*—Orange-white RHS 159C.

*Embryony.*—Monoembryonic.

The tree and its fruit as described herein may vary somewhat in certain characteristics due to climatic and/or soil conditions under which the variety is grown.

What is claimed is:

1. A new and distinct variety of *Citrus reticulata* hybrid tree substantially as herein described and shown.

* * * * *

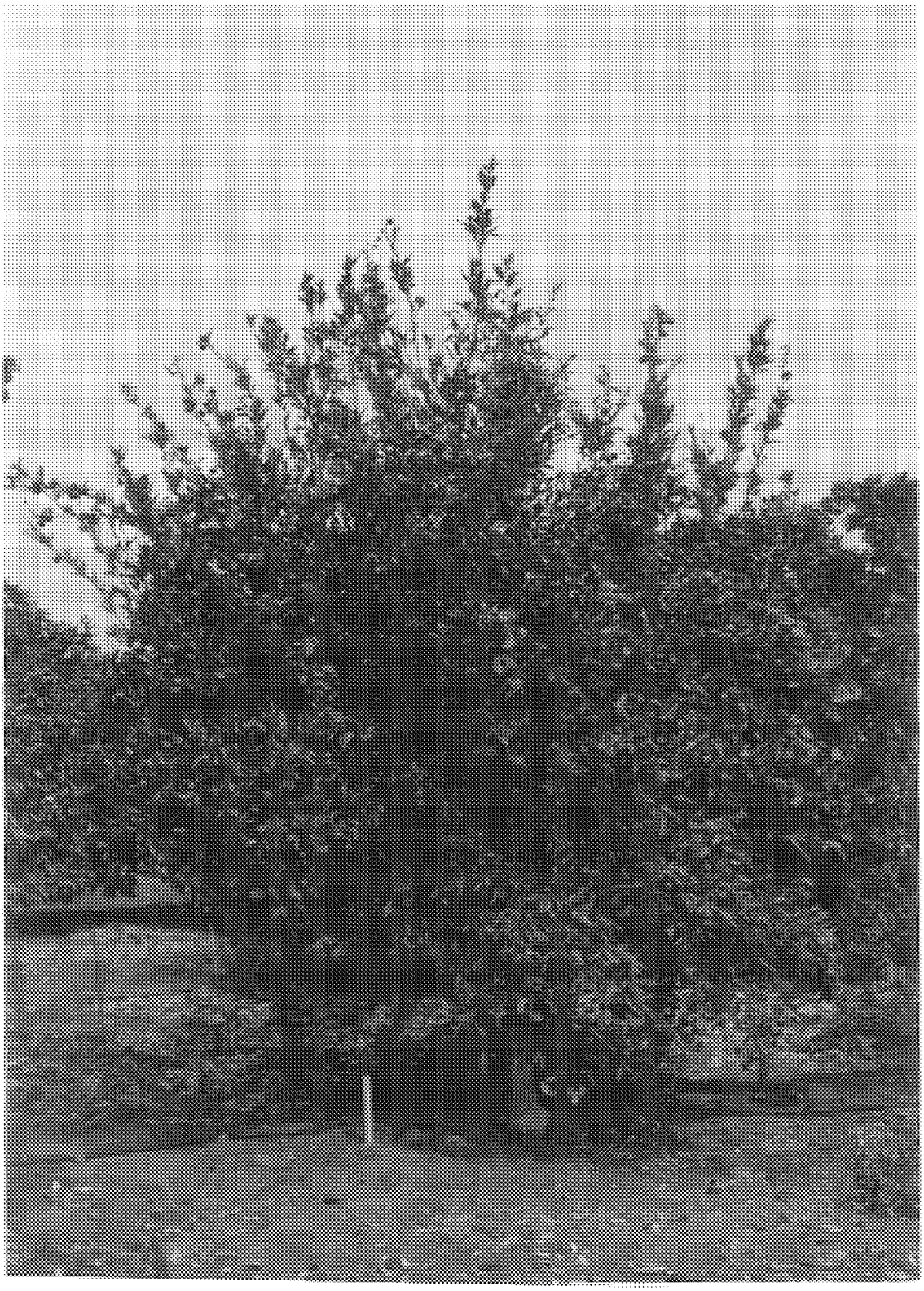

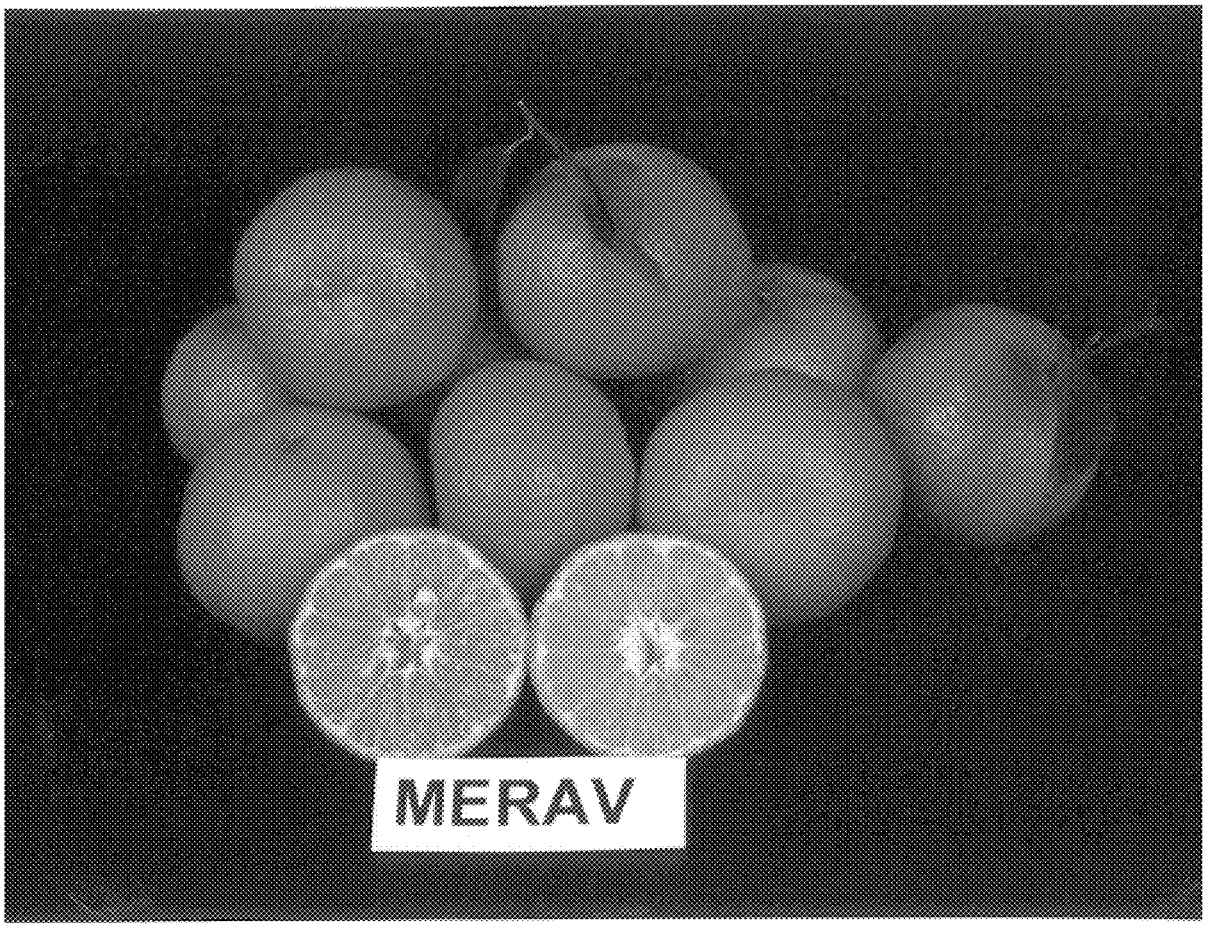
MERAV